(12) United States Patent
Schweitzer et al.

(10) Patent No.: US 11,703,496 B2
(45) Date of Patent: Jul. 18, 2023

(54) MEASURING APPARATUS AND METHOD FOR DETERMINING THE TOTAL ORGANIC CARBON OF A DISSOLVED SAMPLE

(71) Applicant: Endress+Hauser Conducta GmbH+Co. KG, Gerlingen (DE)

(72) Inventors: Daniel Schweitzer, Remshalden (DE); Ulrich Kathe, Ludwigsburg (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 272 days.

(21) Appl. No.: 17/111,155

(22) Filed: Dec. 3, 2020

(65) Prior Publication Data
US 2021/0164956 A1 Jun. 3, 2021

(30) Foreign Application Priority Data
Dec. 3, 2019 (DE) ............. 10 2019 132 869.1

(51) Int. Cl.
*G01N 33/18* (2006.01)
*G01N 27/06* (2006.01)
(Continued)

(52) U.S. Cl.
CPC ......... *G01N 33/1846* (2013.01); *G01N 27/06* (2013.01); *G01N 1/28* (2013.01);
(Continued)

(58) Field of Classification Search
CPC ........ G01N 27/06; G01N 27/07; G01N 27/08; G01N 33/1846; G01N 1/28; G01N 1/44;
(Continued)

(56) References Cited

U.S. PATENT DOCUMENTS 4,749,657 A * 6/1988 Takahashi ............ G01N 31/005
436/52
4,868,127 A * 9/1989 Blades ............... G01N 33/1846
422/186.04

(Continued)

FOREIGN PATENT DOCUMENTS

DE 3535029 A1 4/1986
EP 0150923 B2 10/1995

*Primary Examiner* — Maureen Wallenhorst
(74) *Attorney, Agent, or Firm* — Christopher R. Powers; Endress+Hauser (USA) Holding, Inc.

(57) ABSTRACT

A measuring apparatus for determining the total organic carbon of a sample in a liquid medium includes a reactor block made of a metallic, electrically conductive, and corrosion-resistant material, the reactor block including a housing wall for accommodating a light source, the housing wall including an inlet into and an outlet from the reactor block and a flow chamber in which digestion of the sample for determining the total organic carbon occurs, the flow chamber configured to accommodate the light source and to route the sample to be irradiated with light, wherein the measuring apparatus further includes at least one conductivity measurement device, wherein the reactor block is an external electrode of the conductivity measurement device. A method for determining the total organic carbon of the sample using the measuring apparatus is disclosed.

19 Claims, 1 Drawing Sheet

(51) Int. Cl.
*G01N 27/07* (2006.01)
*G01N 1/28* (2006.01)
*G01N 1/44* (2006.01)
*G01N 27/08* (2006.01)

(52) U.S. Cl.
CPC .............. *G01N 1/44* (2013.01); *G01N 27/07* (2013.01); *G01N 27/08* (2013.01); *Y10T 436/235* (2015.01)

(58) Field of Classification Search
CPC ....... Y10T 436/204998; Y10T 436/235; Y10T 436/25125
USPC ....... 436/133, 146, 147, 149, 150, 151, 175; 422/82.01, 82.02
See application file for complete search history.

(56) References Cited

U.S. PATENT DOCUMENTS

| | | | | |
|---|---|---|---|---|
| 5,275,957 | A | * | 1/1994 | Blades ............... G01N 33/1846 422/78 |
| 6,228,325 | B1 | * | 5/2001 | Godec ................... G01N 27/06 422/80 |
| 7,993,586 | B2 | * | 8/2011 | Fujiyama ............... G01N 27/07 422/68.1 |
| 2003/0211626 | A1 | * | 11/2003 | Davenport ........... G01N 31/005 422/78 |
| 2007/0254374 | A1 | * | 11/2007 | Iharada ............. G01N 33/1846 436/146 |
| 2009/0246882 | A1 | * | 10/2009 | Pochy ................ G01N 33/1826 436/146 |
| 2013/0119266 | A1 | | 5/2013 | Mondt et al. |
| 2016/0084784 | A1 | * | 3/2016 | Rajagopalan ...... G01N 33/1846 324/693 |
| 2020/0003747 | A1 | * | 1/2020 | Rajagopalan ........ G01N 27/045 |

* cited by examiner

MEASURING APPARATUS AND METHOD FOR DETERMINING THE TOTAL ORGANIC CARBON OF A DISSOLVED SAMPLE

CROSS-REFERENCE TO RELATED APPLICATION

The present application is related to and claims the priority benefit of German Patent Application No. 10 2019 132 869.1, filed on Dec. 3, 2019, the entire contents of which are incorporated herein by reference.

TECHNICAL FIELD

The present disclosure relates to a measuring apparatus for determining the total organic carbon of a dissolved sample and to a method for determining with a measuring apparatus the total organic carbon of a sample in a liquid medium.

BACKGROUND

For process water monitoring in the pharmaceutical industry but also in other industries which produce pure water and ultrapure water, it is necessary to measure the total organic carbon (TOC) in liquids in the trace range. In most measuring apparatuses used for this purpose, the organic carbon is converted thermally or by means of UV radiation into $CO_2$ and detected.

In general, one of the following two approaches is used for this purpose:
  (i) Digestion of a defined sample volume and conversion of the resulting amount of $CO_2$ into a gas stream followed by detection of the $CO_2$ concentration in the gas stream in an NDIR (non-dispersive infrared sensor) measuring cell; and
  (ii) Digestion of the liquid by means of UV radiation and measuring the concentration of $CO_2$ dissolved in the liquid by the increased electrical conductivity of the liquid.

In the latter method, the organic carbon is digested into $CO_2$ by UV radiation (in the wavelength range of <200 nm). A vacuum Hg lamp is generally used as the UV source. The $CO_2$ being produced dissolves in the liquid and increases the electrical conductivity. The increase in electrical conductivity correlates with the $CO_2$ concentration in the liquid or with the original carbon concentration or with the proportion of organically bound carbon originally present in the liquid.

According to the state of the art, there are several design variants for implementing the latter method, i.e., digestion of the liquid by means of UV radiation and measuring the concentration of $CO_2$ dissolved in the liquid by the increased electrical conductivity of the liquid. The two most common variants are discontinuous differential conductivity measurement and continuous differential conductivity measurement.

In continuous differential conductivity measurement, measured values are not acquired cyclically as in the discontinuous differential conductivity measurement but continuously. To this end, electrical conductivity is first measured in a first flow conductivity measuring cell. The sample is then digested in a UV flow reactor. Conductivity is then measured again in a second flow conductivity measuring cell. The carbon concentration can be calculated from the increase in conductivity.

A continuous measurement signal is advantageously produced, as a result of which concentration peaks can be reliably detected.

Disadvantageous is that, although the residence time of the sample in the digestion reactor is constant due to the constant sample flow, different organic compounds have different digestion rates. Consequently, the sample may not be completely digested or the degree of digestion between the various substances may differ. Measurement errors can arise as a result.

It is also disadvantageous that digestible compounds, e.g., organic acids, or compounds (e.g., $CHCl_3$) in case of which, in addition to $CO_2$, other conductive and soluble compounds are produced by the digestion contribute to a basic conductivity of the sample and can likewise lead to measurement errors.

Drift of the conductivity measuring cells also leads to measurement errors.

It should also be taken into account that the temperature increase of the liquid (due to the heat of the UV lamp, for example) influences the conductivity, which is why either heat exchangers or the like are necessary to keep both measuring cells at a uniform temperature or a computational temperature compensation is necessary.

Devices known from the prior art for the continuous measurement of organic carbon in liquids require a relatively large installation space on account of components, such as a first conductivity measuring cell, a heat exchanger with applicable heating cartridges or a cooling unit, a digestion reactor, and also a second conductivity measuring cell.

SUMMARY

On the basis of these preliminary considerations, the object of the present disclosure is to improve a measuring apparatus and a method, for example, for the continuous measurement of the total organic carbon (TOC) in liquids, to the effect that at least some of the disadvantages described above are reduced.

The present disclosure achieves this object by the subject matter of claim 1 and also by a method having the features of claim 16.

A measuring apparatus according to the present disclosure for determining the total organic carbon of a sample, for example, one dissolved in a liquid medium, has a reactor block made of electrically conductive and corrosion-resistant material. The material is preferably metallic. Example materials are stainless steel, graphite, titanium, and/or platinum.

The formation of the reactor block from a metal promotes the thermal conductivity of the reactor block.

The reactor block takes the form of a housing with a corresponding housing wall and with an inlet into the reactor block and an outlet from the reactor block.

The reactor block may, for example, take the form of a cube, a cuboid, or a cylinder in which an inlet and an outlet are arranged at defined locations, through which the dissolved sample can be introduced into the measuring apparatus and discharged.

The reactor block can furthermore have a housing wall with a wall thickness of at least 0.5 mm. The wall thickness of the housing wall can also be designed to be at least 15 mm and, as a further example, 21-200 mm thick, as a result of which design-related advantages can arise, e.g., holes of larger diameter in the wall for accommodating measuring components of the corresponding diameter.

The UV lamp heats the reactor block. Optionally, the reactor block may be heated externally or internally or be actively cooled. The relatively large wall thickness of the reactor block allows preheating of the sample or of the liquid medium up to the temperature of the flow chamber through the reactor block itself.

Optionally and advantageously, the reactor block has a first connecting channel in the housing wall, which is arranged parallel to the longitudinal axis of the reactor block. Depending on the wall thickness of the housing wall and the corresponding hole, this first connecting channel can have a diameter of a different size. The arrangement of the first connecting channel in the wall of the reactor block saves additional installation space.

Furthermore, the housing wall encloses a flow chamber in which digestion of the sample for determining the organic carbon occurs. The flow chamber may be a digestion chamber.

The housing wall delimits the flow chamber from the environment. The term "environment" refers to the space outside the reactor block.

The flow chamber is designed to accommodate a light source, for example, a UV light source, and to pass through the sample or the liquid medium with the sample which is to be irradiated with UV light. The UV light source can advantageously be part of the measuring apparatus according to the present disclosure. It can be arranged in the flow chamber so as to be replaceable. The flow chamber can take the form of a self-contained cavity with openings for the passage of liquid media. A plurality of openings may be provided. The UV light source can preferably be a vacuum Hg lamp. UV radiation, preferably in the wavelength range <200 nm, has proven to be favorable.

The measuring apparatus has at least one conductivity measurement device. The conductivity measurement device may consist of one or more components. A plurality of components can be arranged to form a single component composed of several components.

The reactor block is designed as an electrode, for example, as an external electrode of the conductivity measurement device. As a result, the reactor block takes the form of a housing and at the same time an external electrode.

Such a compact arrangement of a measuring apparatus integrating several components into one assembly with the result of increased measurement reliability in the detection of total organic carbon in liquids has previously not been known.

The formation of the reactor block from a metal additionally promotes the thermal conductivity of the reactor block.

The reactor block is designed to absorb heat, which is generated, for example, by the energy of the UV light source in the reactor chamber, and to dissipate it to the environment. As a result, the reactor block is also designed as a heat exchanger to compensate for temperature differences between the conductivity measuring cells integrated in the reactor block and to keep the temperature in the flow chamber of the reactor block constant at defined heat levels.

Advantageous is the arrangement of the first connecting channel in the housing wall of the reactor block because the sample supplied into the first connecting channel can already be preheated to a uniform reactor temperature as a result of the thermal conductivity of the reactor block.

Preheating advantageously reduces the response time of the analyzer, whereby faster response times are possible with limit value monitoring.

Overall, preheating of the sample to the reactor temperature and maintaining a constant temperature in the chamber of the reactor block have a beneficial effect because measurement reliability is increased as a result.

Overall, this also makes it possible to dispense with heat exchangers, heating cartridges, and/or cooling units as separate components.

As a result, the present disclosure advantageously also reduces the installation space required for a measuring apparatus and ensures increased measurement reliability. In addition, the integration of various components in a single assembly makes it possible to manufacture a measuring apparatus in a space-saving manner.

The use of fewer components also advantageously reduces the risk of failure as well as leakages and leaky locations. It is also advantageous that a plurality of functions is integrated into one component, thereby reducing production costs.

The present disclosure is suitable for the use of measurements for determining the concentration of organic compounds in liquids in the trace range.

Advantageous embodiments of the present disclosure are the subject-matter of the dependent claims.

In an advantageous embodiment of the present disclosure, a first conductivity measuring cell of the conductivity measurement device can be arranged in the reactor block with at least two corresponding electrodes, wherein the two electrodes are an internal electrode and an external electrode, and wherein a first internal electrode is arranged within the first conductivity measuring cell and corresponds with the reactor block as an external electrode. The first conductivity measuring cell can be arranged upstream of the flow chamber in which digestion of the sample takes place.

In the aforementioned embodiment, a second conductivity measuring cell of the conductivity measurement device is also arranged with at least two corresponding electrodes, wherein the two electrodes are an internal electrode and an external electrode, and wherein a second internal electrode is arranged within the second conductivity measuring cell and corresponds with the reactor block as an external electrode. The second conductivity measuring cell can be arranged downstream of the flow chamber in which digestion of the sample takes place.

The internal electrodes comprise an electrically conductive material. The temperature inside the two conductivity measuring cells is also uniform on account of their integration in the reactor block.

The first connecting channel may preferably be formed between the inlet and the first conductivity measuring cell. Furthermore, there must be a passage between the first conductivity measuring cell and the flow chamber and a passage between the flow chamber and the second conductivity measuring cell. Lastly, a second connecting channel may be arranged between the second conductivity measuring cell and the outlet.

The second connecting channel may be less than 20% of the length of the first connecting channel.

Advantageously, a supply and discharge device is connected upstream of the inlet of the reactor block. In this case, the supply and discharge device comprises a supply line of the measuring apparatus to a first valve and/or a pump, wherein a third connecting channel extends between the first valve and the pump. A fourth connecting channel is arranged between the pump and the inlet of the reactor block, and a fifth connecting channel is arranged between the outlet of the reactor block and the second valve. Advantageously, a sixth connecting channel extends between the second valve and the first valve. A discharge line is arranged to start from the second valve. The third, fourth, and fifth connecting channels can be formed, for example, by a tube or a hose which extend outside the reactor block.

The supply and discharge device is preferably part of the measuring apparatus. The upstream supply and discharge device expands the measuring apparatus in such a way that a sample can be conveyed through the measuring apparatus in an annular flow or circuit.

Measurement errors caused by different digestion rates can be compensated with an annular flow.

Drift of the conductivity measuring cells can also be corrected by pumping the sample liquid in the circuit until the conductivity in both measuring cells has reached a stable value. This makes it possible to ensure that the sample is completely oxidized.

Drift of the measuring apparatus can occur due to deposits and other effects. However, this can advantageously be corrected. To this end, the evaluation unit is advantageously designed such that an offset measurement, for example, an offset correction, can be carried out during the determination of a measured value.

Useful here is that the first and second valves can be switchable between multiple operating modes. A first operating mode ensures a constant supply into and discharge from the measuring apparatus, and a second operating mode ensures that the medium is returned in the circuit. Valve control based on the respective operating modes can be performed by a control and evaluation unit.

It is also expedient in this respect that the control and evaluation unit also controls the conductivity measurement by the conductivity measurement device, wherein the control and evaluation unit is designed to determine a content of organic carbon in liquid media taking into account the conductivity determined in the first and second conductivity measuring cells.

The flow chamber of the measuring apparatus can be cylindrical. The flow chamber is arranged centrally and parallel to the longitudinal axis of the reactor block and symmetrically to the UV light source and preferably encloses the latter.

The lateral distance between the outer inner wall, facing away from the UV light source, of the lateral surface of the flow chamber and the center of the longitudinal axis of the UV light source, which corresponds to the longitudinal axis of the reactor block, can be less than 8 mm. The lower distance between the outer inner wall of the lower circular section surface of the flow chamber and the lower center of the longitudinal axis of the UV light source can also be less than 8 mm. A sample stream that passes close to the UV light source makes possible an increase in radiation intensity and thus also a complete oxidation of the carbon-containing compounds in the sample.

The first and second conductivity measuring cells may be arranged at the same radial distance from the longitudinal axis of the reactor block.

This arrangement ensures a predictable digestion over the entire vertical lateral surface of the preferably cylindrical flow chamber.

The reactor block can be formed in several parts, thereby facilitating the provision of holes and milled recesses in the production process. As a result, components of the reactor block can also advantageously be replaced more easily in the event of failure.

The reactor block can preferably be made of stainless steel. However, the reactor block may also be made of other metallic materials or metal alloys, e.g., brass or the like, which are electrically conductive and corrosion-resistant. The use of stainless steel as a heat exchanger is known in a wide range of industries, e.g., in condensing boiler technology. Fields of application include the use of heat, heating of a medium, and cooling of a medium. These properties act synergistically in the stainless-steel reactor block in the solution of the inventive task.

Advantageously, the first connecting channel and the second connecting channel, the inlet and the first passage, and the second passage and also the outlet are of equal diameter. This diameter is preferably more than 0.5 mm, particularly preferably between 1.5 and 4 mm.

It is furthermore advantageous that an annular gap is formed in each case between the walls of the first and second conductivity measuring cells and the internal electrode arranged in the respective conductivity measuring cell, and that the first and the second annular gaps have identical volumes and geometric dimensions. The volume and geometric dimension may be equal to the diameter of the first and second connecting channels, of the inlet, of the first and second passages, and of the outlet.

A sealing device, for example, a sleeve that is transparent at least to UV radiation from the UV light source and into which the UV light source is inserted can be arranged in the flow chamber. This allows the UV lamp to be replaced in the event of a defect even if the reactor block is filled with liquid. In this case, the liquid medium with the sample is located between the sealing device and the inner wall of the flow chamber.

It is also advantageous if a third annular gap is arranged between the inner wall of the lateral surface of the flow chamber and the outer wall of the sealing device of the UV light source, said gap having a diameter which is equal to the diameter of the first and second connecting channels and preferably measures between 0.5 and 4 mm. Within this annular gap, the sample flows around the UV light source. The radiation from the UV light source converts the organic components in the sample to $CO_2$. The $CO_2$ forms carbonic acid in the liquid medium, especially, in water, said carbonic acid being detectable with the aid of the conductivity measuring cells as a result of the change in conductivity. At the same time, ozone formation due to overlarge gap widths of the annular gap should be avoided or minimized.

The sample stream, which is ensured in the system and distributed widely over the surface of the UV light source, has an advantageous effect on measurement reliability and measurement accuracy.

A method according to the present disclosure for determining the total organic carbon of a liquid sample, for example, one dissolved in a liquid medium, with a measuring apparatus, for example, with the measuring apparatus according to the present disclosure, comprises the following steps:

I. Providing the measuring apparatus;
  II. Introducing the liquid sample through the inlet of the reactor block into the first connecting channel in which the sample is preheated to the reactor temperature;
  III. Conveying the sample into the first conductivity measuring cell and first measurement of conductivity by the control and evaluation unit;
  IV. Supplying the sample from the first conductivity measuring cell into the flow chamber, in which the sample flows around the UV light source in a third annular gap, wherein radiation from the UV light source digests the sample with the formation of $CO_2$;
  V. Transferring the sample from the flow chamber into the second conductivity measuring cell and performance of the second measurement of conductivity by the control and evaluation unit, and VI. Discharging the sample from the second conductivity measuring cell via the second connecting channel through the outlet of the reactor block.

BRIEF DESCRIPTION OF THE DRAWINGS

Further advantages, features, and details of the present disclosure become apparent from the following description, in which exemplary embodiments of the present disclosure are explained in more detail with reference to the drawings. The person skilled in the art will also expediently consider individually the features disclosed in combination in the drawing, the description, and the claims and combine them into meaningful further combinations. The following are shown:

DETAILED DESCRIPTION

Figure 1:
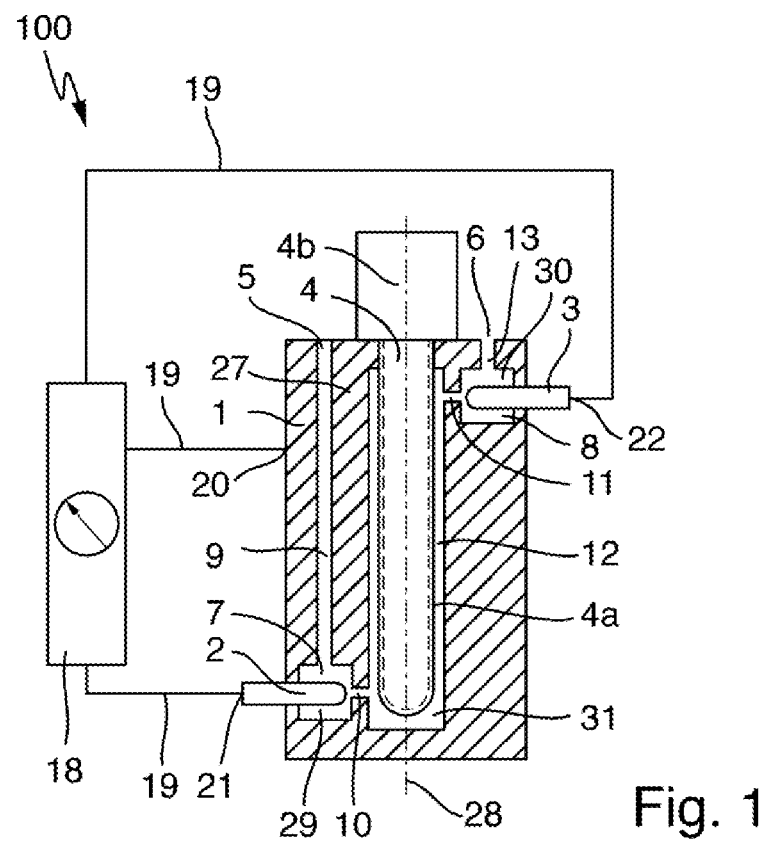
FIG. 1 shows a schematic view of a measuring apparatus in a constant flow mode.

FIG. 1 shows a measuring apparatus 100 for determining the total organic carbon of a sample dissolved in a liquid medium. The measuring apparatus has a reactor block 1.

The reactor block 1 comprises a metallic material and is made of an electrically conductive, corrosion-resistant material, preferably of stainless steel, with a wall thickness of more than 0.5 mm.

The reactor block 1 is designed as an external electrode and is connected to an evaluation unit 18 by a first connection 20 by means of a supply cable 19. The reactor block 1 is designed to absorb and dissipate heat to the outside and thereby acts as a heat exchanger.

The reactor block 1 has a liquid inlet 5 through which the sample is conveyed into a connecting channel 9. The connecting channel 9 is arranged in the wall of the reactor block 1. The heat generated by a UV light source 4 is absorbed by a housing wall 27 of the reactor block 1, whereby the sample introduced into the first connecting channel 9 is preheated to the reactor temperature.

The sample flows from the first connecting channel 9 into a first annular gap 29 of a first conductivity measuring cell 7 and flows around a first internal electrode 2. The first internal electrode 2, which, with the reactor block 1 as an external electrode, corresponds with the control and evaluation unit 18 via the first connection 20 for the supply cable 19, has a second connection 21 for the supply cable 19 to the control and evaluation unit 18. The first internal electrode 2 is inserted in the wall of the reactor block 1, a direct contact and thus a short circuit between the electrodes being prevented as a result of an electrical isolation of the mounting point, e.g., in the form of a polymer seal or a polymer casting. A first measurement of the conductivity of the sample is carried out by the evaluation unit by means of the first internal electrode 2 and the external electrode of the first conductivity measuring cell 7.

From the first conductivity measuring cell 7, the sample is supplied through a first passage 10 into a flow chamber 12 into which the UV light source 4 is introduced in a medium-tight manner. The sample flows around the luminous part of the UV light source 4 in a third annular gap 31 and is digested by the radiation of the UV light source 4.

The UV light source can have a connection head 4b with a seal 4a. The seal 4a can take the form of a quartz glass sleeve with a spherically capped enclosure of the UV light source 4. The seal can also be formed from other materials.

The seal 4a prevents liquid contact with the UV light source 4 and advantageously simplifies replacement of the UV light source.

The sample is transferred through a second passage 11 from the flow chamber 12 into a second annular gap 30 of a second conductivity measuring cell 8 and flows around a second internal electrode 3. The second internal electrode 3, which, with the reactor block 1 as an external electrode, corresponds with the control and evaluation unit 18 via the first connection 20 for the supply cable 19, has a third connection 22 for the supply cable 19 to the evaluation unit 18. The second internal electrode 3 is inserted in the wall of the reactor block 1, a direct contact and thus a short circuit between the electrodes being prevented as a result of an electrical isolation of the mounting point, e.g., in the form of a polymer seal or a polymer casting. By means of the first internal electrode 2 and the reactor block 1 serving as the external electrode of the second conductivity measuring cell 7, a second measurement of the conductivity of the sample is carried out by the evaluation unit 18. The terms "control and evaluation unit" and "evaluation unit" are used synonymously in the present application.

From the second conductivity measuring cell 8, the sample is discharged through a second connecting channel 13 in an outlet 6 of the reactor block 1.

Figure 2:
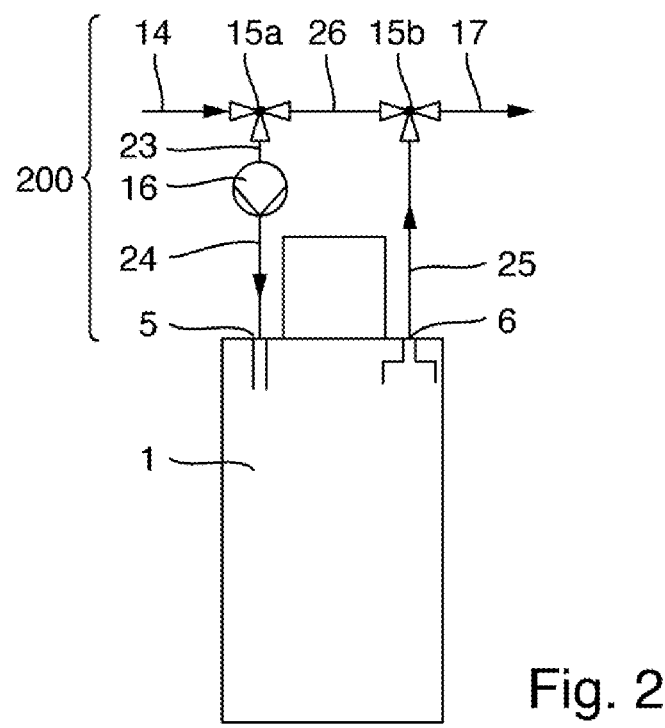
FIG. 2 shows a schematic view of a supply and discharge device as part of the measuring apparatus in an annular flow mode.

FIG. 2 shows a supply and discharge device 200 as part of the measuring apparatus 100 for determining the total organic carbon of a sample dissolved in a liquid medium with a measuring apparatus 100 in an annular flow mode. The internal structure of the reactor block 1 is not shown in FIG. 2 but is constructed analogously to FIG. 1.

In this variant, the sample is conveyed via a supply line 14 to a valve 15a and via a third connecting channel 23 to the pump 16 through the fourth connecting channel 24 into the inlet 5 of the reactor block 1.

The sample passes through the flow chamber in a manner analogous to FIG. 1. After the sample exits the outlet 6, the sample may be returned by means of a pump 16 and the fourth connecting channel 24 to the inlet 5 of the reactor block 1 via a fifth connecting channel 25 via a second valve 15b connected in an annular flow and via a downstream sixth connecting channel 26 via the first valve 15a connected in an annular flow.

As a result, the sample keeps flowing through the reactor chamber in an annular flow or circuit until the conductivity in both conductivity measuring cells 7 and 8 has reached a stable value.

The invention claimed is:

1. A measuring apparatus for determining a total organic carbon content of a sample dissolved in a liquid medium, the measuring apparatus comprising:
   a reactor block made of an electrically conductive and corrosion-resistant material and configured as a housing, which includes a housing wall, which includes an inlet into and an outlet out of the reactor block,
   wherein the housing wall encloses a flow chamber configured to facilitate digestion of the sample to enable determining the total organic carbon therein, wherein a light source is arranged in the flow chamber as to enable a flow of the sample around a luminous section of the light source as to be irradiated with light from the light source; and
   at least one conductivity measurement device disposed in the reactor block and comprising:

an external electrode, wherein the reactor block is configured as the external electrode of the at least one conductivity measurement device;
a first internal electrode disposed within the reactor block upstream of the flow chamber relative to the flow of the sample; and
a second internal electrode disposed within the reactor block downstream of the flow chamber.

2. The measuring apparatus of claim 1, wherein the reactor block comprises a first connecting channel configured to supply the sample from the inlet to the at least one conductivity measurement device, wherein the first connecting channel is defined in the housing wall.

3. The measuring apparatus of claim 1, wherein the first internal electrode is disposed within a first conductivity measuring cell defined within the reactor block upstream of the flow chamber relative to the flow of the sample, and wherein the second internal electrode is disposed within a second conductivity measuring cell defined within the reactor block downstream of the flow chamber.

4. The measuring apparatus of claim 3, wherein:
a first connecting channel is arranged within the housing wall between the inlet and the first conductivity measuring cell, enabling fluid communication therebetween;
a first passage defined in the reactor block enables fluid communication between the first conductivity measuring cell and the flow chamber;
a second passage defined in the reactor block enables fluid communication between the flow chamber and the second conductivity measuring cell; and
a second connecting channel is defined in the reactor block between the second conductivity measuring cell and the outlet, enabling fluid communication therebetween.

5. The measuring apparatus of claim 4, wherein the first connecting channel, the second connecting channel, the inlet, the first passage, the second passage, and the outlet each have a substantially identical diameter.

6. The measuring apparatus of claim 5, wherein the substantially identical diameter is between 1.5 and 4.0 mm.

7. The measuring apparatus of claim 3, wherein the first and the second conductivity measuring cells are arranged at a same radial distance from a longitudinal axis of the reactor block.

8. The measuring apparatus of claim 3, wherein an annular gap is defined each between walls of the first and second conductivity measuring cells and the first and second internal electrodes, respectively, wherein the corresponding annular gaps define substantially identical volumes and geometric dimensions.

9. The measuring apparatus of claim 1, the measuring apparatus further comprising a supply and discharge device disposed upstream of the inlet of the reactor block and configured to define a circuit, wherein the supply and discharge device includes:
a supply line connected to a first valve and a pump, wherein the supply line is configured to supply the sample dissolved in the liquid medium to the measuring apparatus;
a third connecting channel extending between the first valve and the pump;
a fourth connecting channel extending between the pump and the inlet of the reactor block;
a fifth connecting channel extending between the outlet of the reactor block and a second valve;
a sixth connecting channel extending between the second valve and the first valve; and
a discharge line extending from the second valve.

10. The measuring apparatus of claim 9, wherein the first and the second valves are adapted to be switched by a control and evaluation unit of the at least one conductivity measurement device between multiple operating modes of the measuring apparatus, wherein a first operating mode enables a constant supply of the sample into and discharge from the measuring apparatus, and wherein a second operating mode enables a recirculation of the sample through the reactor block via the circuit.

11. The measuring apparatus of claim 1, wherein the at least one conductivity measurement device comprises a control and evaluation unit configured to determine the content of total organic carbon in the sample based on conductivities detected by the at least one conductivity measurement device.

12. The measuring apparatus of claim 11, wherein the control and evaluation unit is configured to perform an offset correction of the detected conductivities when determining a measured value of the total organic carbon content of the sample.

13. The measuring apparatus of claim 1, wherein the flow chamber is cylindrical, wherein the flow chamber is arranged centrally and parallel to a longitudinal axis of the reactor block and symmetrically to the light source as to surround the luminous section of the light source.

14. The measuring apparatus of claim 1, wherein the reactor block is comprised of more than one part and is made of stainless steel.

15. The measuring apparatus of claim 1, wherein a sealing device including a transparent sleeve is disposed in the flow chamber, wherein the sealing device is configured to accept the light source in a replaceable manner.

16. The measuring apparatus of claim 15, wherein a third annular gap is defined between an inner wall of a lateral surface of the flow chamber and an outer surface of the light source or of the sealing device, the third annular gap having a same diameter as a first connecting channel, wherein the first connecting channel is defined in the housing wall and is configured to supply the sample from the inlet to the at least one conductivity measurement device, and wherein the same diameter is greater than 0.5 mm.

17. The measuring apparatus of claim 1, wherein the light source is a UV light source.

18. A method for determining a total organic carbon content of a sample dissolved in a liquid medium, the method comprising:
providing a measuring apparatus comprising:
a reactor block made of an electrically conductive and corrosion-resistant material and configured as a housing which includes a housing wall, which includes an inlet into and an outlet out of the reactor block,
wherein the housing wall encloses a flow chamber configured to enable digestion of the sample as to enable determining the total organic carbon of the sample, wherein a light source is arranged in the flow chamber as to enable a flow of the sample around a luminous section of the light source as to irradiate the sample with light from the light source, and
at least one conductivity measurement device disposed in the reactor block and comprising:
an external electrode, wherein the reactor block is configured as the external electrode of the at least one conductivity measurement device;

a first internal electrode disposed within a first conductivity measuring cell defined within the reactor block upstream of the flow chamber relative to the flow of the sample;

a second internal electrode disposed within a second conductivity measuring cell defined within the reactor block downstream of the flow chamber; and a control and evaluation unit configured to determine the content of total organic carbon in the sample based on conductivities detected by the at least one conductivity measurement device, wherein the housing wall further defines a first connecting channel configured to supply the sample from the inlet to the at least one conductivity measurement device;

introducing the sample through the inlet of the reactor block into the first connecting channel in which the sample is heated to a reactor temperature;

conveying the sample into the first conductivity measuring cell and performing a first measurement of conductivity of the sample using the control and evaluation unit;

supplying the sample from the first conductivity measuring cell into the flow chamber in which the sample flows around the light source in an annular gap between an inner wall of the flow chamber and an outer surface of the light source or of a sealing device in which the light source is disposed, whereby radiation of the light source effects digestion of the sample, resulting in formation of carbon dioxide;

conveying the sample from the flow chamber into the second conductivity measuring cell and performing a second measurement of conductivity of the sample using the control and evaluation unit;

discharging the sample from the second conductivity measuring cell through the outlet of the reactor block; and determining the total organic carbon content of the sample using the first and second measurements of conductivity.

19. The method of claim 18, further comprising continually supplying liquid medium in which the sample is dissolved to the measuring apparatus, wherein the method is performed to generate a continuous differential conductivity measurement to facilitate the determining of the total organic carbon content of the sample.

* * * * *